United States Patent
Ting et al.

(10) Patent No.: US 11,000,570 B2
(45) Date of Patent: *May 11, 2021

(54) ISOFORM NELL-1 PEPTIDE

(71) Applicant: THE REGENTS OF THE UNIVERSITY OF CALIFORNIA, Oakland, CA (US)

(72) Inventors: Kang Ting, Beverly Hills, CA (US); B. Chia Soo, Beverly Hills, CA (US)

(73) Assignee: The Regents of the University of California, Oakland, CA (US)

(*) Notice: Subject to any disclaimer, the term of this patent is extended or adjusted under 35 U.S.C. 154(b) by 81 days.

This patent is subject to a terminal disclaimer.

(21) Appl. No.: 15/954,225

(22) Filed: Apr. 16, 2018

(65) Prior Publication Data

US 2018/0236029 A1    Aug. 23, 2018

Related U.S. Application Data

(60) Continuation of application No. 15/265,680, filed on Sep. 14, 2016, now Pat. No. 9,974,828, which is a division of application No. 13/256,931, filed as application No. PCT/US2010/028540 on Mar. 24, 2010, now Pat. No. 9,447,155.

(60) Provisional application No. 61/163,297, filed on Mar. 25, 2009.

(51) Int. Cl.
| | |
|---|---|
| *A61K 38/17* | (2006.01) |
| *C07K 14/47* | (2006.01) |
| *A61K 35/32* | (2015.01) |
| *A61M 37/00* | (2006.01) |
| *A61N 1/30* | (2006.01) |

(52) U.S. Cl.
CPC ......... *A61K 38/1709* (2013.01); *A61K 35/32* (2013.01); *A61M 37/0092* (2013.01); *A61N 1/303* (2013.01); *C07K 14/47* (2013.01); *A61M 2037/0007* (2013.01)

(58) Field of Classification Search
None
See application file for complete search history.

(56) References Cited

U.S. PATENT DOCUMENTS

| | | |
|---|---|---|
| 7,052,856 B2 | 5/2006 | Ting et al. |
| 7,544,486 B2 | 6/2009 | Ting et al. |
| 7,687,462 B2 | 3/2010 | Ting et al. |
| 7,691,607 B2 | 4/2010 | Ting et al. |
| 7,776,361 B2 | 8/2010 | Ting et al. |

(Continued)

FOREIGN PATENT DOCUMENTS

| | | |
|---|---|---|
| EP | 2411406 B1 | 3/2017 |
| WO | 2004072100 | 8/2004 |

(Continued)

OTHER PUBLICATIONS

Ngo et al., in The Protein Folding Problem and Tertiary Structure Prediction, Merz and Le Grand (Eds), Aug. 1994, Springer Verlag, pp. 433 and 492-495.

(Continued)

*Primary Examiner* — Elizabeth C. Kemmerer
(74) *Attorney, Agent, or Firm* — Taylor English Duma LLP

(57) ABSTRACT

This application is drawn to a method of using an isoform NELL-1 peptide, and compositions thereof for bone formation or for treating, preventing, or ameliorating osteoporosis.

16 Claims, 7 Drawing Sheets

Specification includes a Sequence Listing.

(56) References Cited

U.S. PATENT DOCUMENTS

| | | | |
|---|---|---|---|
| 7,807,787 | B2 | 10/2010 | Ting et al. |
| 7,833,968 | B2 | 11/2010 | Soo et al. |
| 7,884,066 | B2 | 2/2011 | Ting |
| 8,048,646 | B2 | 11/2011 | Ting et al. |
| 8,053,412 | B2 | 11/2011 | Ting et al. |
| 8,207,120 | B2 | 6/2012 | Ting |
| 9,301,976 | B2 | 4/2016 | Soo et al. |
| 9,447,155 | B2 * | 9/2016 | Ting ............... A61K 35/32 |
| 9,598,480 | B2 | 3/2017 | Ting et al. |
| 9,730,965 | B2 | 8/2017 | Soo et al. |
| 9,974,828 | B2 | 5/2018 | Ting |
| 2006/0292670 | A1 | 12/2006 | Kang et al. |
| 2009/0047275 | A1 | 2/2009 | Ting |
| 2012/0065574 | A1 | 3/2012 | Ting et al. |
| 2012/0237560 | A1 | 9/2012 | Soo et al. |
| 2017/0042968 | A1 | 2/2017 | Ting |

FOREIGN PATENT DOCUMENTS

| | | |
|---|---|---|
| WO | 2006089023 | 8/2006 |
| WO | 2008109274 | 9/2008 |
| WO | 2010111421 | 9/2010 |

OTHER PUBLICATIONS

Mok et al., "Evaluation of polyethylene glycol modification of first-generation and helper-dependent adenoviral vectors to reduce innate immune responses", Mol. Ther. 11(1) pp. 66-79 (2005).

Ngo et al., 1994, The Protein Folding Problem and Tertiary Structure Prediction, Merz et al., eds., Birkhauser, Boston, pp. 492-495.

Ting et al., 1999, J. Bone Miner. Res. 14(1):80-89.

Ting, Kang; Applicant-Initiated Interview Summary for U.S. Appl. No. 13/256,931, filed Nov. 23, 2011, dated Mar. 30, 2016, 3 pgs.

Ting, Kang; Final Office Action for U.S. Appl. No. 13/256,931, filed Nov. 23, 2011, dated Jul. 14, 2015, 13 pgs.

Ting, Kang; Issue Notification for U.S. Appl. No. 13/256,931, filed Nov. 23, 2011, dated Aug. 31, 2016, 1 pg.

Ting, Kang; Non-Final Office Action for U.S. Appl. No. 13/256,931, filed Nov. 23, 2011, dated Oct. 26, 2015, 7 pgs.

Ting, Kang; Non-Final Office Action for U.S. Appl. No. 13/256,931, filed Nov. 23, 2011, dated Mar. 26, 2015, 22 pgs.

Ting, Kang; Notice of Allowance for U.S. Appl. No. 13/256,931, filed Nov. 23, 2011, dated May 12, 2016, 12 pgs.

Ting, Kang; Requirement for Restriction/Election for U.S. Appl. No. 13/256,931, filed Nov. 23, 2011, dated Dec. 24, 2014, 9 pgs.

Tokuriki et al., 2009, Curr. Opin. Struct. Biol. 19:596-604.

Ting, Kang; Advisory Action for U.S. Appl. No. 15/265,680, filed Sep. 14, 2016, dated May 25, 2017, 5 pgs.

Ting, Kang; Applicant Initiated Interview Summary for U.S. Appl. No. 15/265,680, filed Sep. 14, 2016, dated Nov. 22, 2017, 3 pgs.

Ting, Kang; Final Office Action for U.S. Appl. No. 15/265,680, filed Sep. 14, 2016, dated Mar. 28, 2017, 12 pgs.

Ting, Kang; Issue Notification for U.S. Appl. No. 15/265,680, filed Sep. 14, 2016, dated May 2, 2018, 1 pg.

Ting, Kang; Non-Final Office Action for U.S. Appl. No. 15/265,680, filed Sep. 14, 2016, dated Nov. 30, 2016, 17 pgs.

Ting, Kang; Non-Final Office Action for U.S. Appl. No. 15/265,680, filed Sep. 14, 2016, dated Aug. 4, 2017, 14 pgs.

Notice of Allowance for U.S. Appl. No. 15/265,680, filed Sep. 14, 2016, dated Jan. 23, 2018, 5 pgs.

Ting, Kang; International Preliminary Report on Patentability for PCT/US2010/028540, filed Mar. 24, 2010, dated Sep. 27, 2011, 6 pgs.

Ting, Kang; International Search Report and Written Opinion for PCT/US2010/028540, filed Mar. 24, 2010, dated Jan. 12, 2011, 10 pgs.

Ting, et al; Human NELL-1 expressed in unilateral coronal synostosis. Journal of Bone and Mineral Research. 1999, vol. 14, No. 1, pp. 80-89.

Aghaloo, T. et al., A study of the role of Nell-1 gene modified goat bone marrow stromal cells in promoting new bone formation, Mol. Ther., Oct. 2007, Vo 1.15, No. 10, pp. 1872-1880.

Aghaloo, T. et al., Nell-I-induced bone regenaration in calvarial defects, The American Journal of Pathology, Sep. 2006, vol. 169, No. 3, pp. 903-915.

Kuroda S. et al., Involvement of epidermal growth factor-like domain of NELL proteins in the novel protein-protein interaction with protein kinase C, Bi ochem. Biophys. Res. Commun., Nov. 30, 1999, vol. 265, No. 3, pp. 752-757.

Ngo, T. et al., "Computational Complexity, Protein Structure Prediction, and the Levinthal Paradox", The Protein ~olding Problem and Tertiary Structure Prediction, Merz et al., eds., Birkhauser, Boston, 1994, pp. 492-495.

Ting, Kang; Supplemental European Search Report for serial No. EP10756811.5, dated Oct. 9, 2012, 2 pgs.

Tokuriki, N. et al., "Stability effects of mutations and protein evolvability", Current Opinion in Structural Biology, 2009, 19: 596-604.

Ting, Kang; Decision to Grant for serial No. 10756811.5, filed Mar. 24, 2010, dated Feb. 2, 2017, 02 pgs.

Ting, Kang; Intention to Grant for serial No. 10756811.5, filed Mar. 24, 2010, dated Sep. 15, 2016, 8 pgs.

Ting, Kang; Office Action for serial No. 10756811.5, filed Mar. 24, 2010, dated Mar. 19, 2015, 4 pgs.

Ting, Kang; Office Action for serial No. 2756168, filed Mar. 24, 2010 dated Mar. 20, 2018, 04 pgs.

Ting, Kang; Office Action for serial No. 2756168, filed Mar. 24, 2010, dated Feb. 26, 2016, 5 pgs.

Ting, Kang; Office Action for serial No. 2756168, filed Mar. 24, 2010, dated Apr. 28, 2017, 4 pgs.

Tan, et al., "The structures of the thrombospondin-1 N-terminal domain and its complex with a synthetic pentameric heparin", Structure, Jan. 2006, vol. 14(1):33-42.

Tolsma, et al., "Peptides derived from two separate domains of the matrix protein thrombospondin-1 have anti-angiogenic activity", J Cell Biol., Jul. 1993, vol. 122(2):497-511.

\* cited by examiner

Sequence of SNELL-1 protein [Homo sapiens] (SEQ ID NO:1)

MDLQELLAKMTAKLNYAETRLSQLENCHCEKTCQVSGLLYRDQDSWVDGDHCRNCTCKSGAVECRRMSCPPLNC
SPDSLPVHIAGQCCKVCRPKCIYGGKVLAEGQRILTKSCRECRGGVLVKITEMCPPLNCSEKDHILPENQCCRV
CRGHNFCAEGPKCGENSECKNWNTKATCECKSGYISVQGDSAYCEDIDECAAKMHYCHANTVCVNLPGLYRCDC
VPGYIRVDDFSCTEHDECGSGQHNCDENAICTNTVQGHSCTCKPGYVGNGTICRAFCEEGCRYGGTCVAPNKCV
CPSGFTGSHCEKDIDECSEGIIECHNHSRCVNLPGWYHCECRSGFHDDGTYSLSGESCIDIDECALRTHTCWND
SACINLAGGFDCLCPSGPSCSGDCPHEGGLKHNGQVWTLKEDRCSVCSCKDGKIFCRRTACDCQNPSADLFCCP
ECDTRVTSQCLDQNGHKLYRSGDNWTHSCQQCRCLEGEVDCWPLTCPNLSCEYTAILEGECCPRCVSDPCLADN
ITYDIRKTCLDSYGVSRLSGSVWTMAGSPCTTCKCKNGRVCCSVDFECLQNN

Figure 6A

Sequence of SNELL-1 DNA (CDS) [homo sapiens] (SEQ ID NO:2)

ATGGATTTACAAGAGCTTTTGGCCAAGATGACTGCAAAACTAAATTATGCAGAGACAAGACTTAGTCAATTGGA
AAACTGTCATTGTGAGAAGACTTGTCAAGTGAGTGGACTGCTCTATCGAGATCAAGACTCTTGGGTAGATGGTG
ACCATTGCAGGAACTGCACTTGCAAAAGTGGTGCCGTGGAATGCCGAAGGATGTCCTGTCCCCCTCTCAATTGC
TCCCCAGACTCCCTCCCAGTGCACATTGCTGGCCAGTGCTGTAAGGTCTGCCGACCAAAATGTATCTATGGAGG
AAAAGTTCTTGCAGAAGGCCAGCGGATTTTAACCAAGAGCTGTCGGGAATGCCGAGGTGGAGTTTTAGTAAAAA
TTACAGAAATGTGTCCTCCTTTGAACTGCTCAGAAAAGGATCACATTCTTCCTGAGAATCAGTGCTGCCGTGTC
TGTAGAGGTCATAACTTTTGTGCAGAAGGACCTAAATGTGGTGAAAACTCAGAGTGCAAAAACTGGAATACAAA
AGCTACTTGTGAGTGCAAGAGTGGTTACATCTCTGTCCAGGGAGACTCTGCCTACTGTGAAGATATTGATGAGT
GTGCAGCTAAGATGCATTACTGTCATGCCAATACTGTGTGTGTCAACCTTCCTGGGTTATATCGCTGTGACTGT
GTCCCAGGATACATTCGTGTGGATGACTTCTCTTGTACAGAACACGATGAATGTGGCAGCGGCCAGCACAACTG
TGATGAGAATGCCATCTGCACCAACACTGTCCAGGGACACAGCTGCACCTGCAAACCGGGCTACGTGGGGAACG
GGACCATCTGCAGAGCTTTCTGTGAAGAGGGCTGCAGATACGGTGGAACGTGTGTGGCTCCCAACAAATGTGTC
TGTCCATCTGGATTCACAGGAAGCCACTGCGAGAAAGATATTGATGAATGTTCAGAGGGAATCATTGAGTGCCA
CAACCATTCCCGCTGCGTTAACCTGCCAGGGTGGTACCACTGTGAGTGCAGAAGCGGTTTCCATGACGATGGGA
CCTATTCACTGTCCGGGGAGTCCTGTATTGACATTGATGAATGTGCCTTAAGAACTCACACCTGTTGGAACGAT
TCTGCCTGCATCAACCTGGCAGGGGGTTTTGACTGTCTCTGCCCCTCTGGGCCCTCCTGCTCTGGTGACTGTCC
TCATGAAGGGGGGCTGAAGCACAATGGCCAGGTGTGGACCTTGAAAGAAGACAGGTGTTCTGTCTGCTCCTGCA
AGGATGGCAAGATATTCTGCCGACGGACAGCTTGTGATTGCCAGAATCCAAGTGCTGACCTATTCTGTTGCCCA
GAATGTGACACCAGAGTCACAAGTCAATGTTTAGACCAAAATGGTCACAAGCTGTATCGAAGTGGAGACAATTG
GACCCATAGCTGTCAGCAGTGTCGGTGTCTGGAAGGAGAGGTAGATTGCTGGCCACTCACTTGCCCCAACTTGA
GCTGTGAGTATACAGCTATCTTAGAAGGGGAATGTTGTCCCCGCTGTGTCAGTGACCCCTGCCTAGCTGATAAC
ATCACCTATGACATCAGAAAAACTTGCCTGGACAGCTATGGTGTTTCACGGCTTAGTGGCTCAGTGTGGACGAT
GGCTGGATCTCCCTGCACAACCTGTAAATGCAAGAATGGAAGAGTCTGTTGTTCTGTGGATTTTGAGTGTCTTC
AAAATAATTGA

Figure 6B

Sequence of LNELL-1 protein [Homo sapiens] ((SEQ ID NO:3)

MPMDLILVVWFCVCTARTVVGFGMDPDLQMDIVTELDLVNTTLGVAQVSGMHNASKAFLFQDIEREIHAA
PHVSEKLIQLFRNKSEFTILATVQQKPSTSGVILSIRELEHSYFELESSGLRDEIRYHYIHNGKPRTEAL
PYRMADGQWHKVALSVSASHLLLHVDCNRIYERVIDPPDTNLPPGINLWLGQRNQKHGLFKGIIQDGKII
FMPNGYITQCPNLNHTCPTCSDFLSLVQGIMDLQELLAKMTAKLNYAETRLSQLENCHCEKTCQVSGLLY
RDQDSWVDGDHCRNCTCKSGAVECRRMSCPPLNCSPDSLPVHIAGQCCKVCRPKCIYGGKVLAEGQRILT
KSCRECRGGVLVKITEMCPPLNCSEKDHILPENQCCRVCRGHNFCAEGPKCGENSECKNWNTKATCECKS
GYISVQGDSAYCEDIDECAAKMHYCHANTVCVNLPGLYRCDCVPGYIRVDDFSCTEHDECGSGQHNCDEN
AICTNTVQGHSCTCKPGYVGNGTICRAFCEEGCRYGGTCVAPNKCVCPSGFTGSHCEKDIDECSEGIIEC
HNHSRCVNLPGWYHCECRSGFHDDGTYSLSGESCIDIDECALRTHTCWNDSACINLAGGFDCLCPSGPSC
SGDCPHEGGLKHNGQVWTLKEDRCSVCSCKDGKIFCRRTACDCQNPSADLFCCPECDTRVTSQCLDQNGH
KLYRSGDNWTHSCQQCRCLEGEVDCWPLTCPNLSCEYTAILEGECCPRCVSDPCLADNITYDIRKTCLDS
YGVSRLSGSVWTMAGSPCTTCKCKNGRVCCSVDFECLQNN

Figure 7A

Sequence of LNELL-1 DNA (CDS) [homo sapiens] (SEQ ID NO:4)

ATGCCGATGGATTTGATTTTAGTTGTGTGGTTCTGTGTGTGCACTGCCAGGACAGTGGTGGGCTTTGGGATGGA
CCCTGACCTTCAGATGGATATCGTCACCGAGCTTGACCTTGTGAACACCACCCTTGGAGTTGCTCAGGTGTCTG
GAATGCACAATGCCAGCAAAGCATTTTTATTTCAAGACATAGAAAGAGAGATCCATGCAGCTCCTCATGTGAGT
GAGAAATTAATTCAGCTGTTCCAGAACAAGAGTGAATTCACCATTTTGGCCACTGTACAGCAGAAGCCATCCAC
TTCAGGAGTGATACTGTCCATTCGAGAACTGGAGCACAGCTATTTTGAACTGGAGAGCAGTGGCCTGAGGGATG
AGATTCGGTATCACTACATACACAATGGGAAGCCAAGGACAGAGGCACTTCCTTACCGCATGGCAGATGGACAA
TGGCACAAGGTTGCACTGTCAGTTAGCGCCTCTCATCTCCTGCTCCATGTCGACTGTAACAGGATTTATGAGCG
TGTGATAGACCCTCCAGATACCAACCTTCCCCAGGAATCAATTTATGGCTTGGCCAGCGCAACCAAAAGCATG
GCTTATTCAAAGGGATCATCCAAGATGGGAAGATCATCTTTATGCCGAATGGATATATAACACAGTGTCCAAAT
CTAAATCACACTTGCCCAACCTGCAGTGATTTCTTAAGCCTGGTGCAAGGAATAATGGATTTACAAGAGCTTTT
GGCCAAGATGACTGCAAAACTAAATTATGCAGAGACAAGACTTAGTCAATTGGAAAACTGTCATTGTGAGAAGA
CTTGTCAAGTGAGTGGACTGCTCTATCGAGATCAAGACTCTTGGGTAGATGGTGACCATTGCAGGAACTGCACT
TGCAAAAGTGGTGCCGTGGAATGCCGAAGGATGTCCTGTCCCCTCTCAATTGCTCCCAGACTCCCTCCCAGT
GCACATTGCTGGCCAGTGCTGTAAGGTCTGCCGACCAAAATGTATCTATGGAGGAAAAGTTCTTGCAGAAGGCC
AGCGGATTTTAACCAAGAGCTGTCGGGAATGCCGAGGTGGAGTTTTAGTAAAAATTACAGAAATGTGTCCTCCT
TTGAACTGCTCAGAAAAGGATCACATTCTTCCTGAGAATCAGTGCTGCCGTGTCTGTAGAGGTCATAACTTTTG
TGCAGAAGGACCTAAATGTGGTGAAAACTCAGAGTGCAAAAACTGGAATACAAAAGCTACTTGTGAGTGCAAGA
GTGGTTACATCTCTGTCCAGGGAGACTCTGCCTACTGTGAAGATATTGATGAGTGTGCAGCTAAGATGCATTAC
TGTCATGCCAATACTGTGTGTGTCAACCTTCCTGGGTTATATCGCTGTGACTGTGTCCCAGGATACATTCGTGT
GGATGACTTCTCTTGTACAGAACACGATGAATGTGGCAGCGGCCAGCACAACTGTGATGAGAATGCCATCTGCA
CCAACACTGTCCAGGGACACAGCTGCACCTGCAAACCGGGCTACGTGGGGAACGGGACCATCTGCAGAGCTTTC
TGTGAAGAGGGCTGCAGATACGGTGGAACGTGTGTGGCTCCCAACAAATGTGTCTGTCCATCTGGATTCACAGG
AAGCCACTGCGAGAAAGATATTGATGAATGTTCAGAGGGAATCATTGAGTGCCACAACCATTCCCGCTGCGTTA
ACCTGCCAGGGTGGTACCACTGTGAGTGCAGAAGCGGTTTCCATGACGATGGGACCTATTCACTGTCCGGGGAG
TCCTGTATTGACATTGATGAATGTGCCTTAAGAACTCACACCTGTTGGAACGATTCTGCCTGCATCAACCTGGC
AGGGGGTTTTGACTGTCTCTGCCCCTCTGGGCCCTCCTGCTCTGGTGACTGTCCTCATGAAGGGGGCTGAAGC
ACAATGGCCAGGTGTGGACCTTGAAAGAAGACAGGTGTTCTGTCTGCTCCTGCAAGGATGGCAAGATATTCTGC
CGACGGACAGCTTGTGATTGCCAGAATCCAAGTGCTGACCTATTCTGTTGCCCAGAATGTGACACCAGAGTCAC
AAGTCAATGTTTAGACCAAAATGGTCACAAGCTGTATCGAAGTGGAGACAATTGGACCCATAGCTGTCAGCAGT
GTCGGTGTCTGGAAGGAGAGGTAGATTGCTGGCCACTCACTTGCCCCAACTTGAGCTGTGAGTATACAGCTATC
TTAGAAGGGGAATGTTGTCCCCGCTGTGTCAGTGACCCCTGCCTAGCTGATAACATCACCTATGACATCAGAAA
AACTTGCCTGGACAGCTATGGTGTTTCACGGCTTAGTGGCTCAGTGTGGACGATGGCTGGATCTCCCTGCACAA
CCTGTAAATGCAAGAATGGAAGAGTCTGTTGTTCTGTGGATTTTGAGTGTCTTCAAAATAATTGA

Figure 7B

SEQUENCE LISTING

```
<160> NUMBER OF SEQ ID NOS: 4

<210> SEQ ID NO 1
<211> LENGTH: 570
<212> TYPE: PRT
<213> ORGANISM: Homo sapiens
<220> FEATURE:
<223> OTHER INFORMATION: Sequence of SNELL-1 protein

<400> SEQUENCE: 1

Met Asp Leu Gln Glu Leu Leu Ala Lys Met Thr Ala Lys Leu Asn Tyr
1               5                   10                  15

Ala Glu Thr Arg Leu Ser Gln Leu Glu Asn Cys His Cys Glu Lys Thr
                20                  25                  30

Cys Gln Val Ser Gly Leu Leu Tyr Arg Asp Gln Asp Ser Trp Val Asp
            35                  40                  45

Gly Asp His Cys Arg Asn Cys Thr Cys Lys Ser Gly Ala Val Glu Cys
        50                  55                  60

Arg Arg Met Ser Cys Pro Pro Leu Asn Cys Ser Pro Asp Ser Leu Pro
65                  70                  75                  80

Val His Ile Ala Gly Gln Cys Cys Lys Val Cys Arg Pro Lys Cys Ile
                85                  90                  95

Tyr Gly Gly Lys Val Leu Ala Glu Gly Gln Arg Ile Leu Thr Lys Ser
                100                 105                 110

Cys Arg Glu Cys Arg Gly Gly Val Leu Val Lys Ile Thr Glu Met Cys
            115                 120                 125

Pro Pro Leu Asn Cys Ser Glu Lys Asp His Ile Leu Pro Glu Asn Gln
        130                 135                 140

Cys Cys Arg Val Cys Arg Gly His Asn Phe Cys Ala Glu Gly Pro Lys
145                 150                 155                 160

Cys Gly Glu Asn Ser Glu Cys Lys Asn Trp Asn Thr Lys Ala Thr Cys
                165                 170                 175

Glu Cys Lys Ser Gly Tyr Ile Ser Val Gln Gly Asp Ser Ala Tyr Cys
            180                 185                 190
```

Glu Asp Ile Asp Glu Cys Ala Ala Lys Met His Tyr Cys His Ala Asn
            195                 200                 205

Thr Val Cys Val Asn Leu Pro Gly Leu Tyr Arg Cys Asp Cys Val Pro
210                 215                 220

Gly Tyr Ile Arg Val Asp Asp Phe Ser Cys Thr Glu His Asp Glu Cys
225                 230                 235                 240

Gly Ser Gly Gln His Asn Cys Asp Glu Asn Ala Ile Cys Thr Asn Thr
            245                 250                 255

Val Gln Gly His Ser Cys Thr Cys Lys Pro Gly Tyr Val Gly Asn Gly
            260                 265                 270

Thr Ile Cys Arg Ala Phe Cys Glu Glu Gly Cys Arg Tyr Gly Gly Thr
            275                 280                 285

Cys Val Ala Pro Asn Lys Cys Val Cys Pro Ser Gly Phe Thr Gly Ser
290                 295                 300

His Cys Glu Lys Asp Ile Asp Glu Cys Ser Glu Gly Ile Ile Glu Cys
305                 310                 315                 320

His Asn His Ser Arg Cys Val Asn Leu Pro Gly Trp Tyr His Cys Glu
            325                 330                 335

Cys Arg Ser Gly Phe His Asp Asp Gly Thr Tyr Ser Leu Ser Gly Glu
            340                 345                 350

Ser Cys Ile Asp Ile Asp Glu Cys Ala Leu Arg Thr His Thr Cys Trp
            355                 360                 365

Asn Asp Ser Ala Cys Ile Asn Leu Ala Gly Gly Phe Asp Cys Leu Cys
370                 375                 380

Pro Ser Gly Pro Ser Cys Ser Gly Asp Cys Pro His Glu Gly Gly Leu
385                 390                 395                 400

Lys His Asn Gly Gln Val Trp Thr Leu Lys Glu Asp Arg Cys Ser Val
            405                 410                 415

Cys Ser Cys Lys Asp Gly Lys Ile Phe Cys Arg Arg Thr Ala Cys Asp
            420                 425                 430

Cys Gln Asn Pro Ser Ala Asp Leu Phe Cys Cys Pro Glu Cys Asp Thr
            435                 440                 445

Arg Val Thr Ser Gln Cys Leu Asp Gln Asn Gly His Lys Leu Tyr Arg
450                 455                 460

Ser Gly Asp Asn Trp Thr His Ser Cys Gln Gln Cys Arg Cys Leu Glu
465                 470                 475                 480

Gly Glu Val Asp Cys Trp Pro Leu Thr Cys Pro Asn Leu Ser Cys Glu
            485                 490                 495

Tyr Thr Ala Ile Leu Glu Gly Glu Cys Cys Pro Arg Cys Val Ser Asp
            500                 505                 510

Pro Cys Leu Ala Asp Asn Ile Thr Tyr Asp Ile Arg Lys Thr Cys Leu
            515                 520                 525

Asp Ser Tyr Gly Val Ser Arg Leu Ser Gly Ser Val Trp Thr Met Ala
530                 535                 540

Gly Ser Pro Cys Thr Thr Cys Lys Cys Lys Asn Gly Arg Val Cys Cys
545                 550                 555                 560

Ser Val Asp Phe Glu Cys Leu Gln Asn Asn
            565                 570

<210> SEQ ID NO 2
<211> LENGTH: 1713
<212> TYPE: DNA
<213> ORGANISM: Homo sapiens
<220> FEATURE:

<223> OTHER INFORMATION: Sequence of SNELL-1 DNA (CDS)

<400> SEQUENCE: 2

```
atggatttac aagagctttt ggccaagatg actgcaaaac taaattatgc agagacaaga      60
cttagtcaat tggaaaactg tcattgtgag aagacttgtc aagtgagtgg actgctctat     120
cgagatcaag actcttgggt agatggtgac cattgcagga actgcacttg caaaagtggt     180
gccgtggaat gccgaaggat gtcctgtccc cctctcaatt gctccccaga ctccctccca     240
gtgcacattg ctggccagtg ctgtaaggtc tgccgaccaa aatgtatcta tggaggaaaa     300
gttcttgcag aaggccagcg gattttaacc aagagctgtc gggaatgccg aggtggagtt     360
ttagtaaaaa ttacagaaat gtgtcctcct ttgaactgct cagaaaagga tcacattctt     420
cctgagaatc agtgctgccg tgtctgtaga ggtcataact tttgtgcaga aggacctaaa     480
tgtggtgaaa actcagagtg caaaaactgg aatacaaaag ctacttgtga gtgcaagagt     540
ggttacatct ctgtccaggg agactctgcc tactgtgaag atattgatga gtgtgcagct     600
aagatgcatt actgtcatgc caatactgtg tgtgtcaacc ttcctgggtt atatcgctgt     660
gactgtgtcc caggatacat tcgtgtggat gacttctctt gtacagaaca cgatgaatgt     720
ggcagcggcc agcacaactg tgatgagaat gccatctgca ccaacactgt ccagggacac     780
agctgcacct gcaaaccggg ctacgtgggg aacgggacca tctgcagagc tttctgtgaa     840
gagggctgca gatacggtgg aacgtgtgtg gctcccaaca aatgtgtctg tccatctgga     900
ttcacaggaa gccactgcga gaaagatatt gatgaatgtt cagagggaat cattgagtgc     960
cacaaccatt cccgctgcgt taacctgcca gggtggtacc actgtgagtg cagaagcggt    1020
ttccatgacg atgggaccta ttcactgtcc ggggagtcct gtattgacat tgatgaatgt    1080
gccttaagaa ctcacacctg ttggaacgat tctgcctgca tcaacctggc aggggggtttt    1140
gactgtctct gccccctctgg gccctcctgc tctggtgact gtcctcatga aggggggctg    1200
aagcacaatg ccaggtgtg gaccttgaaa gaagacaggt gttctgtctg ctcctgcaag    1260
gatggcaaga tattctgccg acggacagct tgtgattgcc agaatccaag tgctgaccta    1320
ttctgttgcc cagaatgtga caccagagtc acaagtcaat gtttagacca aaatggtcac    1380
aagctgtatc gaagtggaga caattggacc catagctgtc agcagtgtcg gtgtctggaa    1440
ggagaggtag attgctggcc actcacttgc cccaacttga gctgtgagta tacagctatc    1500
ttagaagggg aatgttgtcc ccgctgtgtc agtgacccct gcctagctga taacatcacc    1560
tatgacatca gaaaaacttg cctggacagc tatggtgttt cacggcttag tggctcagtg    1620
tggacgatgg ctggatctcc ctgcacaacc tgtaaatgca agaatggaag agtctgttgt    1680
tctgtggatt ttgagtgtct tcaaaataat tga                                 1713
```

<210> SEQ ID NO 3
<211> LENGTH: 810
<212> TYPE: PRT
<213> ORGANISM: Homo sapiens
<220> FEATURE:
<223> OTHER INFORMATION: Sequence of LNELL-1 protein

<400> SEQUENCE: 3

```
Met Pro Met Asp Leu Ile Leu Val Val Trp Phe Cys Val Cys Thr Ala
1               5                   10                  15

Arg Thr Val Val Gly Phe Gly Met Asp Pro Asp Leu Gln Met Asp Ile
            20                  25                  30

Val Thr Glu Leu Asp Leu Val Asn Thr Thr Leu Gly Val Ala Gln Val
```

```
                35                  40                  45
Ser Gly Met His Asn Ala Ser Lys Ala Phe Leu Phe Gln Asp Ile Glu
 50                  55                  60

Arg Glu Ile His Ala Ala Pro His Val Ser Glu Lys Leu Ile Gln Leu
 65                  70                  75                  80

Phe Arg Asn Lys Ser Glu Phe Thr Ile Leu Ala Thr Val Gln Gln Lys
                 85                  90                  95

Pro Ser Thr Ser Gly Val Ile Leu Ser Ile Arg Glu Leu Glu His Ser
                100                 105                 110

Tyr Phe Glu Leu Glu Ser Ser Gly Leu Arg Asp Glu Ile Arg Tyr His
                115                 120                 125

Tyr Ile His Asn Gly Lys Pro Arg Thr Glu Ala Leu Pro Tyr Arg Met
            130                 135                 140

Ala Asp Gly Gln Trp His Lys Val Ala Leu Ser Val Ser Ala Ser His
145                 150                 155                 160

Leu Leu Leu His Val Asp Cys Asn Arg Ile Tyr Glu Arg Val Ile Asp
                165                 170                 175

Pro Pro Asp Thr Asn Leu Pro Pro Gly Ile Asn Leu Trp Leu Gly Gln
                180                 185                 190

Arg Asn Gln Lys His Gly Leu Phe Lys Gly Ile Ile Gln Asp Gly Lys
            195                 200                 205

Ile Ile Phe Met Pro Asn Gly Tyr Ile Thr Gln Cys Pro Asn Leu Asn
210                 215                 220

His Thr Cys Pro Thr Cys Ser Asp Phe Leu Ser Leu Val Gln Gly Ile
225                 230                 235                 240

Met Asp Leu Gln Glu Leu Leu Ala Lys Met Thr Ala Lys Leu Asn Tyr
                245                 250                 255

Ala Glu Thr Arg Leu Ser Gln Leu Glu Asn Cys His Cys Glu Lys Thr
                260                 265                 270

Cys Gln Val Ser Gly Leu Leu Tyr Arg Asp Gln Asp Ser Trp Val Asp
            275                 280                 285

Gly Asp His Cys Arg Asn Cys Thr Cys Lys Ser Gly Ala Val Glu Cys
        290                 295                 300

Arg Arg Met Ser Cys Pro Pro Leu Asn Cys Ser Pro Asp Ser Leu Pro
305                 310                 315                 320

Val His Ile Ala Gly Gln Cys Cys Lys Val Cys Arg Pro Lys Cys Ile
                325                 330                 335

Tyr Gly Gly Lys Val Leu Ala Glu Gly Gln Arg Ile Leu Thr Lys Ser
            340                 345                 350

Cys Arg Glu Cys Arg Gly Gly Val Leu Val Lys Ile Thr Glu Met Cys
        355                 360                 365

Pro Pro Leu Asn Cys Ser Glu Lys Asp His Ile Leu Pro Glu Asn Gln
            370                 375                 380

Cys Cys Arg Val Cys Arg Gly His Asn Phe Cys Ala Glu Gly Pro Lys
385                 390                 395                 400

Cys Gly Glu Asn Ser Glu Cys Lys Asn Trp Asn Thr Lys Ala Thr Cys
                405                 410                 415

Glu Cys Lys Ser Gly Tyr Ile Ser Val Gln Gly Asp Ser Ala Tyr Cys
            420                 425                 430

Glu Asp Ile Asp Glu Cys Ala Ala Lys Met His Tyr Cys His Ala Asn
        435                 440                 445

Thr Val Cys Val Asn Leu Pro Gly Leu Tyr Arg Cys Asp Cys Val Pro
450                 455                 460
```

```
Gly Tyr Ile Arg Val Asp Asp Phe Ser Cys Thr Glu His Asp Glu Cys
465                 470                 475                 480

Gly Ser Gly Gln His Asn Cys Asp Glu Asn Ala Ile Cys Thr Asn Thr
            485                 490                 495

Val Gln Gly His Ser Cys Thr Cys Lys Pro Gly Tyr Val Gly Asn Gly
        500                 505                 510

Thr Ile Cys Arg Ala Phe Cys Glu Glu Gly Cys Arg Tyr Gly Gly Thr
            515                 520                 525

Cys Val Ala Pro Asn Lys Cys Val Cys Pro Ser Gly Phe Thr Gly Ser
530                 535                 540

His Cys Glu Lys Asp Ile Asp Glu Cys Ser Gly Ile Ile Glu Cys
545                 550                 555                 560

His Asn His Ser Arg Cys Val Asn Leu Pro Gly Trp Tyr His Cys Glu
                565                 570                 575

Cys Arg Ser Gly Phe His Asp Asp Gly Thr Tyr Ser Leu Ser Gly Glu
            580                 585                 590

Ser Cys Ile Asp Ile Asp Glu Cys Ala Leu Arg Thr His Thr Cys Trp
        595                 600                 605

Asn Asp Ser Ala Cys Ile Asn Leu Ala Gly Gly Phe Asp Cys Leu Cys
610                 615                 620

Pro Ser Gly Pro Ser Cys Ser Gly Asp Cys Pro His Glu Gly Gly Leu
625                 630                 635                 640

Lys His Asn Gly Gln Val Trp Thr Leu Lys Glu Asp Arg Cys Ser Val
                645                 650                 655

Cys Ser Cys Lys Asp Gly Lys Ile Phe Cys Arg Arg Thr Ala Cys Asp
            660                 665                 670

Cys Gln Asn Pro Ser Ala Asp Leu Phe Cys Cys Pro Glu Cys Asp Thr
        675                 680                 685

Arg Val Thr Ser Gln Cys Leu Asp Gln Asn Gly His Lys Leu Tyr Arg
690                 695                 700

Ser Gly Asp Asn Trp Thr His Ser Cys Gln Gln Cys Arg Cys Leu Glu
705                 710                 715                 720

Gly Glu Val Asp Cys Trp Pro Leu Thr Cys Pro Asn Leu Ser Cys Glu
                725                 730                 735

Tyr Thr Ala Ile Leu Glu Gly Glu Cys Cys Pro Arg Cys Val Ser Asp
            740                 745                 750

Pro Cys Leu Ala Asp Asn Ile Thr Tyr Asp Ile Arg Lys Thr Cys Leu
        755                 760                 765

Asp Ser Tyr Gly Val Ser Arg Leu Ser Gly Ser Val Trp Thr Met Ala
770                 775                 780

Gly Ser Pro Cys Thr Thr Cys Lys Cys Lys Asn Gly Arg Val Cys Cys
785                 790                 795                 800

Ser Val Asp Phe Glu Cys Leu Gln Asn Asn
                805                 810

<210> SEQ ID NO 4
<211> LENGTH: 2433
<212> TYPE: DNA
<213> ORGANISM: Homo sapiens
<220> FEATURE:
<223> OTHER INFORMATION: Sequence of LNELL-1 DNA (CDS)

<400> SEQUENCE: 4
atgccgatgg atttgatttt agttgtgtgg ttctgtgtgt gcactgccag gacagtggtg      60
```

```
ggctttggga tggaccctga ccttcagatg gatatcgtca ccgagcttga ccttgtgaac    120
accacccttg gagttgctca ggtgtctgga atgcacaatg ccagcaaagc attttattt      180 caagacatag aaagagagat ccatgcagct cctcatgtga gtgagaaatt aattcagctg    240
ttccagaaca agagtgaatt caccattttg gccactgtac agcagaagcc atccacttca    300
ggagtgatac tgtccattcg agaactggag cacagctatt ttgaactgga gagcagtggc   360
ctgagggatg agattcggta tcactacata cacaatggga agccaaggac agaggcactt    420
ccttaccgca tggcagatgg acaatggcac aaggttgcac tgtcagttag cgcctctcat   480
ctcctgctcc atgtcgactg taacaggatt tatgagcgtg tgatagaccc tccagatacc    540
aaccttcccc caggaatcaa tttatggctt ggccagcgca accaaaagca tggcttattc     600
aaagggatca tccaagatgg gaagatcatc tttatgccga atggatatat aacacagtgt    660
ccaaatctaa atcacacttg cccaacctgc agtgatttct taagcctggt gcaaggaata    720
atggatttac aagagctttt ggccaagatg actgcaaaac taaattatgc agagacaaga    780
cttagtcaat tggaaaactg tcattgtgag aagacttgtc aagtgagtgg actgctctat   840
cgagatcaag actcttgggt agatggtgac cattgcagga actgcacttg caaaagtggt    900
gccgtggaat gccgaaggat gtcctgtccc cctctcaatt gctccccaga ctccctccca    960
gtgcacattg ctggccagtg ctgtaaggtc tgccgaccaa aatgtatcta tggaggaaaa    1020
gttcttgcag aaggccagcg gattttaacc aagagctgtc gggaatgccg aggtggagtt    1080
ttagtaaaaa ttacagaaat gtgtcctcct ttgaactgct cagaaaagga tcacattctt    1140
cctgagaatc agtgctgccg tgtctgtaga ggtcataact tttgtgcaga aggacctaaa    1200
tgtggtgaaa actcagagtg caaaaactgg aatacaaaag ctacttgtga gtgcaagagt    1260
ggttacatct ctgtccaggg agactctgcc tactgtgaag atattgatga gtgtgcagct    1320
aagatgcatt actgtcatgc caatactgtg tgtgtcaacc ttcctgggtt atatcgctgt    1380
gactgtgtcc caggatacat tcgtgtggat gacttctctt gtacagaaca cgatgaatgt    1440
ggcagcggcc agcacaactg tgatgagaat gccatctgca ccaacactgt ccagggacac    1500
agctgcacct gcaaaccggg ctacgtgggg aacgggacca tctgcagagc tttctgtgaa    1560
gagggctgca gatacggtgg aacgtgtgtg ctcccaacaa atgtgtctg tccatctgga     1620 ttcacaggaa gccactgcga gaaagatatt gatgaatgtt cagagggaat cattgagtgc    1680
cacaaccatt cccgctgcgt taacctgcca gggtggtacc actgtgagtg cagaagcggt    1740
ttccatgacg atgggaccta ttcactgtcc ggggagtcct gtattgacat tgatgaatgt    1800
gccttaagaa ctcacacctg ttggaacgat tctgcctgca tcaacctggc aggggtttt    1860 gactgtctct gcccctctgg gccctcctgc tctggtgact gtcctcatga aggggggctg    1920
aagcacaatg ccaggtgtg gaccttgaaa gaagacaggt gttctgtctg ctcctgcaag    1980
gatggcaaga tattctgccg acggacagct tgtgattgcc agaatccaag tgctgaccta    2040
ttctgttgcc cagaatgtga caccagagtc acaagtcaat gtttagacca aaatggtcac    2100
aagctgtatc gaagtggaga caattggacc catagctgtc agcagtgtcg gtgtctggaa    2160
ggagaggtag attgctggcc actcacttgc cccaacttga gctgtgagta cagctatc    2220 ttagaagggg aatgttgtcc ccgctgtgtc agtgacccct gcctagctga taacatcacc    2280
```

```
tatgacatca gaaaaacttg cctggacagc tatggtgttt cacggcttag tggctcagtg    2340
tggacgatgg ctggatctcc ctgcacaacc tgtaaatgca agaatggaag agtctgttgt    2400
tctgtggatt ttgagtgtct tcaaaataat tga                                 2433
```

ISOFORM NELL-1 PEPTIDE

STATEMENT AS TO RIGHTS TO INVENTIONS MADE UNDER FEDERALLY SPONSORED RESEARCH AND DEVELOPMENT

This invention was made with Government support under DE016107, awarded by the National Institutes of Health. The Government has certain rights in the invention.

BACKGROUND OF THE INVENTION

There are many situations where bone formation and regeneration are required for treatment, e.g., alveolar bone grafting, craniofacial distraction osteogenesis, spinal fusion, segmental long bone defects.

Defects in the process of bone formation and regeneration are linked to the development of several human diseases and disorders, e.g. osteoporosis and osteogenesis imperfecta. Failure of the bone repair or cartilage repair mechanism is also associated with significant complications in clinical orthopedic practice, for example, fibrous non-union following bone fracture, implant interface failures and large allograft failures. The lives of many individuals would be improved by the development of new therapies designed to stimulate and strengthen the fracture repair process.

Any new technique to stimulate bone repair or cartilage repair would be a valuable tool in treating bone fractures. A significant portion of fractured bones are still treated by casting, allowing natural mechanisms to effect wound repair. Although there have been advances in fracture treatment in recent years, including improved devices, the development of new processes to stimulate or complement the wound repair mechanisms would represent significant progress in this area.

The techniques of bone reconstruction, such as used to reconstruct defects occurring as a result of trauma, cancer surgery or errors in development, would be improved by new methods to promote bone repair. Reconstructive methods currently employed, such as using autologous bone grafts or bone grafts with attached soft tissue and blood vessels, are associated with significant drawbacks of both cost and difficulty. For example, harvesting a useful amount of autologous bone is not easily achieved, and even autologous grafts often become infected or suffer from resorption.

Readily available and reliable bone graft material is essential for many orthopedic surgeries. The current gold standard for bone graft material is autologous bone. However associated donor site morbidity including pain, gait disturbance, thigh paresthesia for iliac crest donor sites, infection, neurologic deficits, and hematomas for calvarial grafts make autograft harvest less than ideal. Thus, there is a need for better autograft alternatives.

Efforts to influence bone repair using bone stimulating proteins and peptides, e.g., bone morphogenic proteins (BMPs), resulted in only limited success. While BMP2 is FDA approved and clinically successful as an osteoinductive biologic, there are significant reported side effects including life-threatening cervical swelling. Therefore there is need to develop improved and safer therapeutic approaches.

Cartilage is a type of dense connective tissue. It is composed of chondrocytes which are dispersed in a firm gel-like matrix. Cartilage is avascular (contains no blood vessels) and nutrients are diffused through the matrix. Cartilage is found in the joints, the rib cage, the ear, the nose, the throat, and between intervertebral disks.

Cartilage can be damaged by wear, injury, or diseases. As aging progresses, the water and protein content of the body's cartilage changes. This change results in weaker, more fragile and thin cartilage. Osteoarthritis is a common condition of cartilage failure that can lead to limited range of motion, bone damage and invariably pain. Due to a combination of acute stress and chronic fatigue, osteoarthritis directly manifests itself in a wearing away of the articulating surface and, in extreme cases, bone can be exposed in the joint. In another example, loss of the protective stabilizing meniscus leads to increased joint laxity or abnormal motions that lead to joint instability. The excessive motion and narrowed contact area promotes early arthritic changes.

Although numerous methods have been described for treatment of cartilage problems, it is clear that many are artificial or mechanically based solutions that do not seek to recreate normal cartilage tissue biology. Therefore, there is a need for methods for stimulating cartilage formation and repair.

Efforts have been continuously made to find better or alternative osteoinductive agents and therapeutic approaches in treating bone related and cartilage related conditions.

SUMMARY OF THE INVENTION

This invention provides an isoform Nell-1 (ISN-1) peptide and methods of making the isoform Nell-1 peptide.

In various embodiments, this invention provides a composition or a bone graft for enhancing the bone formation in a subject in which it is implanted. In some embodiments, the composition contains a biocompatible matrix and an ISN-1 peptide, a related agent, or combination thereof. The composition can further comprise LNell-1 protein, a related agent, or a combination thereof.

In some embodiments, the composition can be a pharmaceutical composition which comprises a suitable carrier or excipient. In some embodiments, the pharmaceutical composition can be formulated into suitable formulation for suitable route of administration.

In some embodiments, the composition can be a bone graft which contains a biocompatible matrix and an ISN-1 protein, a related agent, a cell expressing an ISN-1 protein, or a combination thereof. In some embodiments, the graft material is resorbable or biodegradable. In some embodiments, the graft material can be synthetic or naturally occurring (e.g., allograft). The matrix can include a biodegradable polymer. The matrix can be impregnated with an ISN-1 protein or a related agent, a cell expressing an ISN-1 protein or a related agent, or a combination thereof. The bone graft material can further comprise LNell-1 protein or a related agent, a cell expressing LNell-1 protein or a related agent, or a combination thereof.

In various embodiments, this invention provides a method of increasing bone formation or regeneration. The method can be used for the repair of bone fractures. The method comprises increasing concentration of an ISN-1 gene product at or near the fracture site. In some embodiments, the method comprises introducing an osteogenic cell or bone precursor cell that over expresses ISN-1 into the fracture site. In some embodiments, the method comprises increasing the expression of ISN-1 gene product in an osteogenic cell or bone precursor cell at or near the site of the bone fracture.

In some embodiments, the fracture site is contacted with an ISN-1 protein or a pharmaceutical composition thereof. The fracture site can be contacted with LNell-1 protein in addition to the ISN-1 protein.

In various embodiments, this invention provides a method of treating osteoporosis using an ISN-1, a related agent, or a composition thereof.

In various embodiments, this invention provides a method for inducing cartilage formation or repair using an ISN-1, a related agent, or a composition thereof. The composition can include an ISN-1 or related agent, and optionally at least one other active agent, cells, and biocompatible material implanted for the purpose of cartilage repair (i.e., hyaline cartilage, elastic cartilage, or fibrocartilage).

In various embodiments, the use of ISN-1 can be combined with the use of LNell-1.

In various embodiments, this invention provides a method of expressing a functional ISN-1 peptide in a cell, said method comprising providing a nucleic acid construct including at least a nucleic acid encoding at least an ISN-1 peptide in frame with a nucleic acid encoding a secretory signal peptide; transfecting a cell with said nucleic acid construct; culturing said cell under conditions that permit expression of the ISN-1 peptide; optionally collecting ISN-1 peptide secreted from the cell line; optionally substantially purifying the ISN-1 peptide; and optionally testing the activity of the ISN-1 peptide to induce bone formation.

Related cell line and nucleic acid construct for expressing ISN-1 are also provided.

In the aforementioned embodiments, the ISN-1 protein can be SNell-1 protein.

BRIEF DESCRIPTION OF THE DRAWINGS

FIG. 6A shows sequence of SNell-1 protein [*Homo sapiens*] (SEQ ID NO:1).

FIG. 6B shows sequence of SNell-1 DNA (CDS) [*Homo sapiens*] (SEQ ID NO:2).

FIG. 7A shows sequence of LNell-1 protein [*Homo sapiens*] (SEQ ID NO:3).

FIG. 7B shows sequence of LNell-1 DNA (CDS) [*Homo sapiens*] (SEQ ID NO:4).

DETAILED DESCRIPTION

Figure 1:
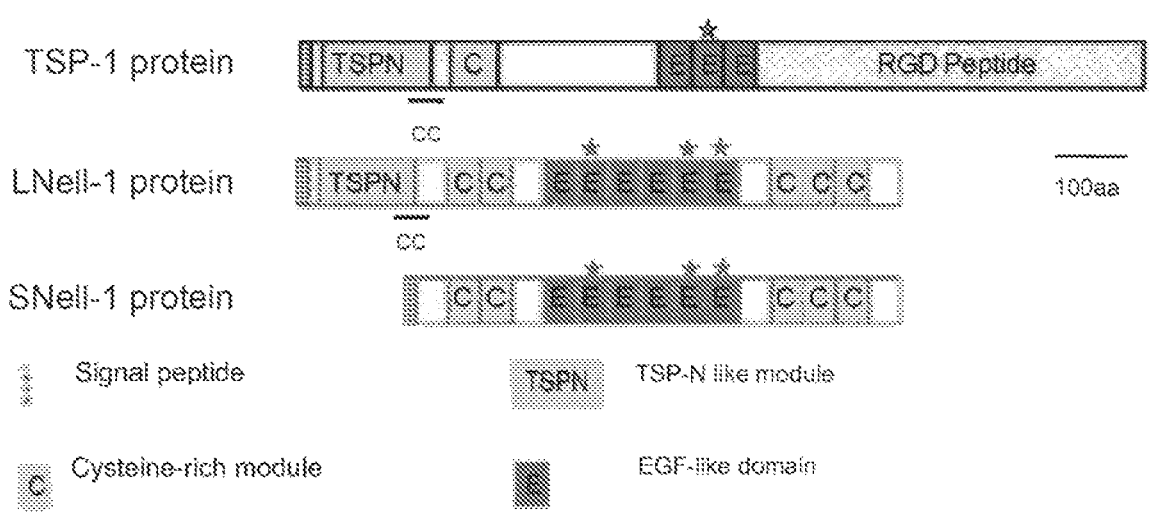
FIG. 1 shows schematic comparison of TSP-1 with LNell-1 and SNell-1 proteins.

The present invention provides an isoform Nell-1 peptide (generally referred as ISN-1 herein). The previously discovered Nell-1 peptide of 810 amino acids is referred to as LNell-1 herein. One exemplary ISN-1 is a short peptide referred to as SNell-1 herein.

Definition

As used herein, the term "ISN-1" refers to a Nell-1 peptide where the TSP1-N [N-terminal thrombospondin-1 (TSP-1)-like domain present in Nell-1 peptide is removed so as to be a peptide retaining the function of Nell-1 having a molecular weight about 63 kD. Physical advantages of a peptide having a lower molecular weight include, e.g., enhanced efficiency of delivery into a cell, ease of upstream process development—more efficient cell synthesis or secretion into media, ease of downstream process development—more efficient separation, purification, folding, etc. Biological advantages include increased osteogenic differentiation as evidenced by increased expression of osteoblastic differentiation markers Runx2, Osx, and Oc (FIG. 3) and bone formation.

The term "osteogenic cells" refers to cells capable of mineralizing. Osteogenic cells include osteoblasts, osteoblast like cells, mesenchymal cells, fibroblast cells, fetal embryonic cells, stem cells, bone marrow cells, dura cells, chrondrocytes, and chondroblastic cells.

As used herein, the term "bone precursor cells" refers to the cells that can differentiate into osteoblasts upon exposure to a bone growth factor and deposit calcium into the extracellular matrix.

As used herein, the term "bone progenitor cells" refers to any or all of those cells that have the capacity to ultimately form, or contribute to the formation of, new bone tissue. This includes various cells in different stages of differentiation, such as, for example, stem cells, bone marrow cells, fibroblast cells, vascular cells, osteoblast cells, chondroblast cells, osteoclast cells, and the like. Bone progenitor cells also include cells that have been isolated and manipulated in vitro, e.g. subjected to stimulation with agents such as cytokines or growth factors or even genetically engineered cells. The particular type or types of bone progenitor cells that are stimulated using the methods and compositions of the invention are not important, so long as the cells are stimulated in such a way that they are activated and, in the context of in vivo embodiments, ultimately give rise to new bone tissue.

The term "osteochondroprogenitor" refers to any cell capable of forming cartilage, e.g., less differentiated osteogenic cells which are capable of mineralizing and/or forming cartilage. Osteochondroprogenitor cells include osteoblasts, osteoblast like cells, mesenchymal cells, fibroblast cells, fetal embryonic cells, stem cells, bone marrow cells, dura cells, chrondrocytes, and chondroblastic cells.

The term "osteoporosis" refers to a heterogeneous group of disorders characterized by decreased bone mass and fractures. Clinically, osteoporosis is segregated into type I and type II. Type I osteoporosis occurs predominantly in middle aged women and is associated with estrogen loss at the menopause, while osteoporosis type II is associated with advancing age.

The term "cartilage" refers to all forms of cartilage including, but not limited to, hyaline, elastic, and fibrocartilage.

The term "nucleic acid" or "oligonucleotide" herein refers to at least two nucleotides covalently linked together. A nucleic acid of the present invention is preferably single-stranded or double stranded and will generally contain phosphodiester bonds, although in some cases, as outlined below, nucleic acid analogs are included that can have alternate backbones, comprising, for example, phosphoramide, phosphorothioate, phosphorodithioate, O-methylphophoroamidite linkages, and peptide nucleic acid backbones and linkages. Other analog nucleic acids include those with positive backbones, non-ionic backbones, and non-ribose backbones. Nucleic acids containing one or more carbocyclic sugars are also included within the definition of nucleic acids. Modifications of the ribose-phosphate backbone can be done to facilitate the addition of additional moieties such as labels, or to increase the stability and half-life of such molecules in physiological environments.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

The term "cell adhesion molecules" refers collectively to laminins, fibronectin, vitronectin, vascular cell adhesion molecules (V-CAM) and intercellular adhesion molecules (I-CAM) and collagen.

The terms "carrier," or "pharmaceutically acceptable carrier," or "delivery vehicle," or "vehicle" can be used interchangeably.

The terms "increasing", "enhancing", and "facilitating" may be used interchangeably.

As used herein, the term "Nell-1 peptide" can include a Nell-1 related agent. For example, a Nell-1 peptide related agent can include any polypeptide with significant homology to a Nell-1 peptide or a fragment thereof. Significant homology can be a homology of higher than about 50% homology to a Nell-1 peptide, e.g., higher than about 60% homology to a Nell-1 peptide, higher than about 70% homology to a Nell-1 peptide, or higher than about 80% homology to a Nell-1 peptide. Nell-1 peptide may be referred simply as Nell peptide herein.

The Nell-1 peptides can be natural and/or recombinant Nell-1 peptides with a non-mutated wild-type sequence or recombinant Nell-1 peptides with a mutated wild-type sequence that still contains significant homology to Nell-1 peptides. In addition, Nell-1 peptides can be derived from, but not limited to, an organism such as human cells, bacteria, yeast, or insect or plant cells. In some embodiments, the term "Nell-1 peptide" includes structural, functional or conformational equivalents of Nell-1 peptide. As used herein, a structural equivalent of a Nell-1 peptide refers to a protein or peptide including a structure equivalent or substantially similar to that of a Nell-1 peptide or of a functional domain of a Nell-1 peptide. A functional equivalent of a Nell-1 peptide refers to a protein or peptide having a function equivalent or substantially similar to that of a Nell peptide or of a functional domain of a Nell-1 peptide. A conformational equivalent of a Nell-1 peptide refers to a protein or peptide having a conformation equivalent or substantially similar to that of a Nell-1 peptide or of a functional domain of a Nell-1 peptide.

In some embodiments, the Nell-1 peptide described herein can be a derivative of the Nell-1 peptide. The term "derivative" as used herein, refers to any chemical or biological compounds or materials derived from a Nell-1 peptide, structural equivalents thereof, or conformational equivalents thereof. For example, such a derivative can include any pro-drug form, PEGylated form, or any other form of a Nell peptide that renders the Nell-1 peptide more stable or to have a better osteophilicity or lipophilicity. In some embodiments, the derivative can be a Nell-1 peptide attached to poly(ethylene glycol), a poly(amino acid), a hydrocarbyl short chain having C1-C20 carbons, or a biocompatible polymer. In some embodiments, the term "derivative" can include a Nell-1 peptide mimetics. Synthesis of mimetics of a peptide is well documented in the art.

In some embodiments, the peptide derivative described herein includes a physically or chemically modified Nell-1 peptide. Physically modified peptide can be modification by, for example, modification by ionic force such as forming an ionic pair with a counterion, modification by hydrogen bonding, modification by modulation of pH, modulation by solvent selection, or modification by using different protein folding/unfolding procedures, which can involve selection of folding/unfolding temperature, pH, solvent, and duration at different stage of folding/unfolding.

In some embodiments, the peptide derivative can include a chemically modified Nell-1 peptide. For example, a short hydrocarbon group(s) (e.g. methyl or ethyl) can be selectively attached to one or multiple sites on the Nell-1 peptide molecule to modify the chemical and/or physical properties of the peptide. In some embodiments, a mono-, oligo- or poly(ethylene glycol) (PEG) group(s) can be selectively attached to one or multiple sites on the Nell-1 peptide molecule to modify the chemical and/or physical properties of the peptide by commonly known protein PEGylation procedures (see, e.g., Mok, H., et al., Mol. Ther., 11(1):66-79 (2005)).

In the same vein, isoform Nell-1 peptide can include an isoform Nell-1 related agent or derivative. The above described principles are applicable to the isoform Nell-1 peptide.

Isoform Nell-1 Peptides

Nell-I peptide, an 810 amino acid peptide with a molecular weight of 90 kD, has been found to have osteoinductive properties. Nell-I peptide, methods of its expression and use in treating bone and cartilage related conditions have been described in U.S. Pat. Nos. 7,052,856, 7,544,486, 7,776,361, 7,687,462, 7,691,607, 7,884,066, and 7,833,968 and U.S. application Ser. No. 11/973,831, published as U.S. 2009/0047275.

The isoform Nell-1 in the present invention does not include the Nell-1 described in the previous patents or patent applications identified above.

Isoform Nell-1 (referred to as ISN-1 herein) is a Nell-1 peptide lacking a TSP1-N [N-terminal thrombospondin-1 (TSP-1)-like domain present in LNell-1. One exemplary ISN-1 is a short Nell-1 (SNell-1) of sequence of SEQ ID NO:1.

Rat or mouse isoform Nell-1 peptides share ~93% predicted amino acid homology with human Nell-1. LNell-1 contains several highly conserved motifs including a secretory signal peptide, an N-terminal thrombospondin-1 (TSP1-N)-like module (also described as laminin G-like domain), five chordin-like cysteine-rich (CR) domains (also known as von Willebrand factor type C domains) and six epidermal growth factor (EGF)-like domains. Rat LNell-1 is secreted into media as 400-kDa proteins that convert to 130-kDa proteins after prolonged denaturation. The 130-kDa monomers are assumed to associate into homotrimers via either the coiled-coil region or CR domains. The EGF-like domains interact with and are phosphorylated by protein kinase C (PKC) in a PKC isoform specific manner. (FIG. 1)

Human LNell-1 contains 810 amino acids with a molecular weight of 89.5 kD (~120 kD after post-translational modification). LNell-1 is transcribed from the proximal alternative promoter (AP-L).

SNell-1 was predicted to have 570 aa with a molecular weight of 62.5 kD. SNell-1 is transcribed from a novel alternative promoter (AP-S). Both AP-L and AP-S contain multiple functional regulatory elements for binding Runx2 (e.g., OSE2) and Osx [e.g., specificity protein 1 (SP1)].

Runx2 promotes LNell-1 and SNell-1 mRNA/protein expression, while Osx induces SNell-1 mRNA/protein, but suppresses LNell-1 mRNA expression, indicating that LNell-1 and SNell-1 have distinct roles at early and late stages respectively of osteoblast differentiation. Moreover, LNell-1 can reciprocally downregulate Osx transcription, while SNell-1 can upregulate both Runx2 and Osx transcripts and increases osteoblastic differentiation. Like LNell-1, SNell-1 is expressed during skeletal growth and demonstrates osteogenic potential in vitro and in vivo.

Both Nell-1 isoforms can be required during osteogenesis. LNell-1 and SNell-1 have distinct, non-overlapping functions during osteogenesis and chondrogenesis. SNell-1, which upregulates both Runx2 and Osx, is believed to be an even more potent osteoinductive agent than LNell-1.

SNell-1 peptide is of a sequence of SEQ ID NO:1. SNell-1 peptide is encoded by a DNA sequence of SEQ ID NO:2. LNell-1 peptide is of a sequence of SEQ ID NO:3. LNell-1 peptide is encoded by a DNA sequence of SEQ ID NO:4.

Method of Increasing Bone Formation and Regeneration

This invention provides a method of increasing bone formation and regeneration. The method can be used for bone fracture repair. The method is useful in a variety of contexts including, but are not limited to, bone reconstruction of defects occurring as a result of trauma, cancer surgery or errors in development, treatment of osteogenesis imperfecta, treatment of osteoporosis, and the healing of major or minor bone fractures.

The method for bone fracture repair comprises increasing concentration of an ISN-1 gene product at or near the fracture site. In some embodiments, the method comprises transfecting an osteogenic cell with a vector that expresses ISN-1 protein or a related agent at or near the bone fracture site. In some embodiments, the method comprises introducing an osteogenic cell or bone precursor cell that overexpresses ISN-1 into the fracture site.

In another approach to fracture repair, the fracture site is contacted with an ISN-1 protein. In some embodiments, the fracture site is contacted with LNell-1 in addition to an ISN-1 protein. The protein can be produced by a cell (e.g. introduced by introduction of a cell overexpressing Nell-1 protein), or by administration of the protein alone or in combination with a pharmacological excipient, or by administration of a "naked DNA" vector capable of expressing Nell-1 peptide or the ISN-1. The ISN-1 protein can be a component of a bone repair/bone graft material and/or part of a prosthetic device.

In some embodiments, in a manner analogous to the use of bone morphogenic proteins (e.g. BMP-1 through BMP-24), the ISN-1 can be used to speed repair of bone fractures or to induce bone repair or replacement under circumstances where natural healing is limited or non-existent. In general, such methods involve increasing the amount of a Nell-1 gene product at or near the fracture site in a bone. The ISN-1 gene product concentration can be increased by one or more of a number of methods. In one approach, cells at or near the bone fracture site are induced to express elevated levels of ISN-1. This can be accomplished in vivo, for example, by the use of modulators of Nell-1 expression, by altering the ISN-1 promoter, or by transfecting the cell with a construct that expresses ISN-1. This also can be accomplished by modifying such cells to overexpress Nell-1 ex vivo and then introduced back into the subject organism (e.g. at or near a fracture site).

In various embodiments, this invention provides a method of facilitating bone formation or regeneration, the method comprising increasing the concentration of an ISN-1 gene product in an osteogenic cell. The ISN-1 gene product can be an ISN-1 peptide, a related agent, or a combination thereof. In some embodiments, the osteogenic cell can be a mature osteoblast, osteoblast, a mesenchymal cell, a fibroblast cell, a fetal embryonic cell, a stem cell, a bone marrow cell, a dura cell, a chrondrocyte, and a chondroblast.

In some embodiments, the increasing concentration of an ISN-1 gene product comprises transfecting an osteogenic cell with a vector that expresses an ISN-1 protein or a related agent. In some embodiments, the increasing concentration of an ISN-1 gene product comprises administering to the bone fracture site with a composition comprising an ISN-1 protein or a related agent. The composition can further comprise a pharmaceutically acceptable carrier.

In various embodiments, the use of ISN-1 and LNell-1 can be combined. It is expected that ISN-1 and LNell-1 can work in synergy and the combination provides improvement to the existing approaches.

In various embodiments, the isoform Nell-1 can be SNell-1.

Method of Treating Osteoporosis

The use of Nell-I for treating, preventing, and ameliorating osteoporosis has been described in U.S. Pat. No. 7,884,066, the teaching of which is incorporated by reference herein.

In various embodiments, this invention provides a method of treating, preventing or ameliorating osteoporosis by administering to a bone tissue at a pre-selected site an effective amount of an ISN-1 or related agent.

In some embodiments, the method can further comprise applying to the pre-selected site a physical force to disperse the ISN-1 or related agent. In some embodiments, the physical force can be ultrasound.

In some embodiments, the administering step comprises: making an incision in the bone tissue at the pre-selected site, and delivering to the bone tissue at the pre-selected site via the incision.

In some embodiments, the ISN-1 or related agent is formulated into a formulation suitable for a mode of delivery selected from percutaneous injection through intact skin to a site, direct injection through a surgically opened site or a trauma site, surgical implantation, extravascular delivery, extravascular injection, extravascular catheter based injection, intravascular delivery, intravascular injection, intravascular catheter based injections, intravenous delivery, intravenous injection, intravenous catheter based injections, intraarterial delivery, intraarterial injection, intraarterial catheter based injections, intrathecal delivery, intrathecal injection, intrathecal catheter based injections, intraosseous delivery, intraosseous injection, catheter based injections, intracartilaginous delivery, intracartilaginous injection, intracartilaginous catheter based injections, intravesical delivery, intravesical injection, intravesical catheter based injection, delivery via a mechanical pump with a percutaneous or implantable catheter, catheter based delivery to an area or organ in the body, or delivery via expanded dispersion through a device that increases tissue penetration or wider tissue distribution. In some embodiments, the device provides ultrasound, iontophoresis, heat or pressure.

In various embodiments, the use of ISN-1 and LNell-1 can be combined. It is expected that ISN-1 and LNell-1 can work in synergy and the combination provides improvements to the existing approaches. In various embodiments, the isoform Nell-1 can be SNell-1.

Method of Inducing Cartilage Formation and Regeneration

The use of Nell-I for inducing cartilage formation and regeneration has been described in U.S. Pat. No. 7,687,462, the teaching of which is incorporated by reference herein.

In various embodiments, the present invention provides agents and methods for inducing cartilage formation or repair using an ISN-1 peptide or a related agent (collectively referred as "agent"). The composition can include an ISN-1 peptide, a related agent, and optionally at least one other active agent, cells, and biocompatible material implanted for the purpose of cartilage repair (i.e., hyaline cartilage, elastic cartilage, or fibrocartilage).

In some embodiments, the present invention provides a composition that contains an effective amount of at least one agent for either directly or indirectly promoting the generation of cartilage for treating, preventing or ameliorating a cartilage related medical condition. One of the agents for direct promotion of cartilage generation can be ISN-1 peptides or ISN-1 based gene therapy or ISN-1 gene product enhancers applied to chondrogenic cells such as, but not limited to, chondroblasts, chondrocytes, or chondroprogenitor cells, adult and embryonic stem cells, bone marrow cells, bone marrow stromal cells, mesenchymal cells, a fibroblast, or adipose derived cells. The agent for indirect promotion of cartilage generation (e.g., through inducing chondroblast/chondrocyte differentiation) can be, e.g., one of Nell peptide, or agonists of Nell peptide receptors.

In some embodiments, the composition can include, e.g., one or more inhibitors or antagonists of ISN-1 peptide receptors, high dose ISN-1 peptides, or combinations thereof. Such a composition is effective for inhibition of chondrogenic differentiation by inhibiting potential or committed chondrogenic cells such as, but not limited to, osteoblasts, osteoprogenitor cells, stem cells, bone marrow cells, fibroblastic cells, dural cells, periosteal cells, pericytes, and/or muscle cells.

In various embodiments, the use of ISN-1 and LNell-1 can be combined. It is expected that ISN-1 and LNell-1 can work in synergy and the combination provides improvements to the existing approaches. In various embodiments, the isoform Nell-1 can be SNell-1.

Composition

In various embodiments, this invention provides a composition useful for facilitating bone formation or regeneration. The composition comprises an ISN-1 peptide, an ISN-1 related agent, or a combination thereof.

The composition can be a pharmaceutical composition which comprises a pharmaceutically acceptable carrier. The pharmaceutically acceptable carrier can be a carrier for a mode of delivery of oral administration, topical administration, in situ implant, intravenous administration, parenteral administration, local administration, intra-arterial injection, injection into a fracture site, and delivery in a biodegradable matrix. In the various embodiments, the composition can further comprise LNell-1 protein, a related agent, or a combination thereof.

The pharmaceutical composition can be formulated into a formulation suitable for a mode of delivery selected from percutaneous injection through intact skin to a site, direct injection through a surgically opened site or a trauma site, surgical implantation, extravascular delivery, extravascular injection, extravascular catheter based injection, intravascular delivery, intravascular injection, intravascular catheter based injections, intravenous delivery, intravenous injection, intravenous catheter based injections, intraarterial delivery, intraarterial injection, intraarterial catheter based injections, intrathecal delivery, intrathecal injection, intrathecal catheter based injections, intraosseous delivery, intraosseous injection, catheter based injections, intracartilaginous delivery, intracartilaginous injection, intracartilaginous catheter based injections, intravesical delivery, intravesical injection, intravesical catheter based injection, delivery via a mechanical pump with a percutaneous or implantable catheter, catheter based delivery to an area or organ in the body, or delivery via expanded dispersion through a device that increases tissue penetration or wider tissue distribution.

In various embodiments, the use of ISN-1 and LNell-1 can be combined. ISN-1 and LNell-1 can be used in the same fashion or substantially the same fashion. It is expected that ISN-1 and LNell-1 can work in synergy and the combination provides improvements to the existing approaches. In various embodiments, the isoform Nell-1 can be SNell-1.

Bone Graft

In various embodiments, the composition can be a bone graft material. In various embodiments, this invention provides a bone graft material for enhancing bone formation in the animal in which it is implanted.

In some embodiments, the bone graft material contains a biocompatible matrix and an ISN-1 protein, a related agent, or a combination thereof. In some embodiments, the graft material can be resorbable or biodegradable or biostable. In some embodiments, the graft material can be synthetic or naturally occurring (e.g., allograft). The matrix can include a biodegradable polymer or a biostable polymer and can be impregnated with an ISN-1 protein, a related agent, and/or a cell expressing an ISN-1 protein or a related agent. The biocompatible matrix can comprise collagen. The biocompatible matrix can comprise a bioglass or a bioceramics. The biocompatible matrix can comprise a cell adhesion molecule.

In some embodiments, the ISN-1 protein is produced by a cell within the matrix expressing the ISN-1 protein or a related agent, which are exogenous. In some embodiments, the ISN-1 protein is provided via pharmaceutical composition. In the aforementioned embodiments, the bone graft material can further comprise LNell-1 protein, a related agent, or a combination thereof.

An exemplary bone graft material comprises a collagen conjugate containing (e.g. from about 0.001 to about 99.999 weight percent) collagen having dispersed substantially uniformly therein; and (e.g. about 99.999 to about 0.001 weight percent) an ISN-1 protein, a related agent, and/or a cell expressing an ISN-1 protein or a related agent. In some embodiments, the graft material includes collagen and/or demineralized or non-demineralized bone fragments in addition to the ISN-1 protein or cells expressing an ISN-1 protein.

Cells expressing or over expressing ISN-1 can be incorporated into such bone graft materials or ISN-1 polypeptides can be incorporated into such bone graft materials. These graft materials can be used in the treatment of fractures or to facilitate the replacement/healing of prostheses or bone transplants.

In various embodiments, the use of ISN-1 and LNell-1 can be combined. It is expected that ISN-1 and LNell-1 can work in synergy and the combination provides improvements to the existing approaches. In various embodiments, the isoform Nell-1 can be SNell-1.

Method of Making Isoform Nell-1 Peptide

The expression and purification of Nell-I peptide has been described in U.S. Pat. Nos. 7,544,486 and 7,691,507, the teachings of which are incorporated by reference herein.

This invention provides methods for the expression and purification of the isoform Nell-1. In various embodiments, this invention provides nucleic acid constructs expressing ISN-1 and cells expressing ISN-1 peptides which may be useful in producing quantities of ISN-1 peptides. In some embodiments, the nucleic acid constructs expressing ISN-1 may further include nucleic acid sequences encoding signal peptides which may facilitate the protein trafficking and post production modification of the ISN-1 in the host cell. In some embodiments, the signal peptide may facilitate the secretion of the peptide from the host cell.

In various embodiments, this invention provides a method of expressing a functional ISN-1 peptide in a cell, said method comprising: providing a nucleic acid construct including at least a nucleic acid encoding at least an ISN-1 peptide in frame with a nucleic acid encoding a secretory signal peptide; transfecting a cell with said nucleic acid construct; culturing said cell under conditions that permit expression of the ISN-1 peptide; optionally collecting ISN-1 peptide secreted from the cell line; optionally substantially purifying the ISN-1 peptide; and optionally testing the activity of the ISN-1 peptide to induce bone formation.

In various embodiments, this invention provides a nucleic acid construct for expressing an ISN-1 peptide in a cell, said nucleic acid construct comprising at least a nucleic acid encoding at least an ISN-1 peptide in frame with a nucleic acid encoding a secretory signal peptide.

In various embodiments, this invention provides a cell line for expressing a functional ISN-1 peptide, said cell line including a nucleic acid construct comprising at least a nucleic acid encoding at least an ISN-1 peptide in frame with a nucleic acid encoding a secretory signal peptide.

In some embodiments, the secretory signal peptide is an insect secretory peptide. In some embodiments, the secretory signal peptide is a Nell peptide signal sequence. In some embodiments, the secretory signal peptide is selected from the group consisting of a melittin signal sequence, a drosphila immunoglobulin-binding protein signal sequence, an equine interferon-gamma (elFN-gamma) signal peptide, a snake phospholipase A2 inhibitor signal peptide, a human lysozyme signal peptide, and a chicken lyzozyme signal peptide.

In the aforementioned embodiments, the cell can be a mammalian cell or an insect cell. Said insect cell can be a high five cell. Said mammalian cell can be a COS7 cell. In the aforementioned embodiments, the secretory signal peptide can be a Nell peptide signal sequence. In the aforementioned embodiments, the ISN-1 peptide can be SNell-1.

In various embodiments, the isoform Nell-1 can be SNell-1.

U.S. Pat. Nos. 7,052,856, 7,544,486, 7,776,361, 7,687,462, 7,691,607, 7,884,066, and 7,833,968 and U.S. application Ser. No. 11/973,831, published as U.S. 2009/0047275, describe Nell-I peptide, compositions thereof, its expression and purification, and its use in bone fracture repair including facilitating bone formation and increasing bone mineralization, treating osteoporosis, and inducing cartilage formation and regeneration. These patents or applications provide the state of art which contributes to the enablement to various aspects of the present invention.

EMBODIMENTS

The method of bone formation and repair generally involves increasing ISN-1 protein concentration in a bone progenitor cell or contacting a cell (e.g. a bone progenitor cell) with an ISN-1 polypeptide or with a vector encoding an ISN-1 polypeptide.

This can be accomplished by transforming a bone precursor cell so that it expresses elevated levels of endogenous ISN-1 or so that it expresses ISN-1 from an exogenous transfected ISN-1 nucleic acid.

This also can be accomplished by contacting bone precursor cells at or near the bone, bone fracture site, or cartilage disease site with an ISN-1 protein or a composition thereof or local administration of an ISN-1 protein or a composition thereof.

A) Transformation of Cells to Increase ISN-1 Production

In a more preferred embodiment, the ISN-1 gene expressing nucleic acids (e.g. cDNA(s)) can be cloned into gene therapy vectors that are competent to transfect cells (such as human or other mammalian cells) in vitro and/or in vivo. The methods and procedures of such cloning and cell transfection are described in U.S. Pat. No. 7,052,856, the teachings of which are incorporated herein in their entirety by reference.

B) Administration of Exogenously Produced ISN-1

1) Delivery of ISN-1 to Target Cells

ISN-1 proteins or related agents can be prepared for intravenous, parenteral, topical, oral, or local administration (e.g. by aerosol or transdermally). Particularly preferred modes of administration include intra-arterial injection, injection into fracture sites or delivery in a biodegradable matrix. The ISN-1 proteins agents can be combined with a pharmaceutically acceptable carrier, which can be referred to as carrier or excipient, to form a pharmacological composition.

Various pharmaceutically suitable formulations, earners, other additives, and administering routes are described in U.S. Pat. Nos. 7,776,361, 7,884,066, and 7,833,968 and U.S. application Ser. No. 11/973,831, published as U.S. 2009/0047275, which are incorporated herein by reference.

2) Bone Graft Materials

ISN-1 protein can be applied directly to a bone or bone fracture site. This can be accomplished during surgery (e.g. when setting complex fractures, when reconstructing bone, when performing bone transplants, etc.) or can be accomplished by direct injection.

In certain preferred embodiments, particularly where bone reconstruction or repair is performed surgically, it is desired to administer the ISN-1 protein using a sustained delivery "vehicle". Sustained delivery vehicles include, but are not limited to biodegradable delivery vehicles. Biodegradable delivery vehicles are preferably porous. Various delivery vehicles are described in U.S. Pat. Nos. 7,776,361, 7,884,066, and 7,833,968, and U.S. application Ser. No. 11/973,831, published as U.S. 2009/0047275, which are incorporated herein by reference.

Other delivery vehicles include, but are not limited to bone graft materials. Bone graft materials can be derived from natural materials (e.g. transplanted bone or bone fragments), synthetic materials (e.g. various polymers and/or ceramics) or combinations of both. Bone graft materials are typically utilized to fill voids or otherwise replace lost bone material. Such graft materials are also often provided as components of prosthetic devices (e.g. bone replacements or supports) to facilitate tight bonding/annealing of the prosthetic with the living bone. The bone graft material can include a biodegradable polymer or a biostable polymer.

Bone grafts using bioactive glasses and calcium phosphates, collagen, mixtures and the like have good biocompatibility and give rise to bone tissue formation and incorporation in some cases. Various bone graft materials are described in U.S. Pat. Nos. 7,776,361, 7,884,066, and 7,833,968, and U.S. application Ser. No. 11/973,831, published as U.S. 2009/0047275, which are incorporated herein by reference.

The bone graft material can further include bone morphogenic proteins (BMP) or other bioactive agents such as cell adhesion molecules. Particularly suitable graft materials include, for example, isolated mineralized cancellous bone sections, powders or granules of mineralized bone, demineralized cancellous bone sections, powders or granules of demineralized bone, guanidine-HCl extracted demineralized bone matrix, sintered cortical or cancellous bone, coralline hydroxyapatite sold by Interpore under the trade name Interpore 500, and granular ceramics such as that incorporated into the bone graft substitute Collagraft sold by Zimmer, or filamentous sponges such as those made from collagen by Orquest.

In various embodiments, the ISN-1 proteins, BMP, or other bioactive agent can be bound to the substrate of the bone graft materials.

3) ISN-1 for Osteoporosis

In some embodiments, the ISN-1 protein described herein can be used to treat, prevent, or ameliorate osteoporosis. In this embodiment, the ISN-1 peptide can be administered to a site of osteoporosis. Subsequently, a physical force such as a vibration or ultrasound can be applied to the site of administration to disperse the ISN-1 peptide. In some embodiments, the ISN-1 peptide can be administered to the site of osteoporosis by the acts of (a) making an incision in a tissue (bone) and (b) delivering to the tissue through the incision the ISN-1 peptide. In some embodiments, the Nell-1 peptide can be in a pharmaceutically acceptable carrier for sustained delivery.

4) ISN-1 for Cartilage Regeneration

In the present invention, the isoform Nell-1 peptide can be used to treat, prevent, or ameliorate cartilage degeneration. In one embodiment, the ISN-1 peptide can be administered to a site of fibrocartilage disease such as spinal disc disease with or without a pharmaceutically acceptable carrier, with or without other devices (e.g., disc nucleus replacement device, allograft device, or cells) or biological factors (e.g., LIM-1 protein). In another embodiment, the ISN-1 peptide can be administered to a site of fibrocartilage disease such as meniscus, with or without a pharmaceutically acceptable carrier, with or without other devices (e.g., meniscus allograft or meniscus scaffold or prosthesis, or cells) or biological factors. In another embodiment, the SNell-1 peptide can be administered to a site of hyaline cartilage disease such as knee articular cartilage, with or without a pharmaceutically acceptable carrier, with or without other devices (e.g., cartilage allograft or cartilage scaffold or prosthesis) or biological factors. In another embodiment, the ISN-1 peptide can be administered to another site of hyaline cartilage disease such as tracheal cartilage (e.g., tracheomalacia), with or without a pharmaceutically acceptable carrier, with or without other devices (e.g., cartilage allograft or cartilage scaffold or prosthesis) or biological factors.

In other embodiments, the ISN-1 peptide can be administered to a site of elastic cartilage disease such as auricular or epiglottis with or without a pharmaceutically acceptable carrier, with or without other devices (e.g., cells) or biological factors.

A composition described herein can be formulated into formulations suitable for any suitable mode of administration/delivery to a mammalian subject (e.g., a human being). An ordinary artisan with the teachings above can formulate the composition described here into any desirable formulation by using, e.g., an appropriate carrier with an appropriate amount of an ISN-1 peptide or a related agent defined above.

Some examples of delivering the composition can be, e.g., percutaneous injection through intact skin to various sites, or direct injection through nonintact skin (e.g., surgically opened sites or trauma sites). In some embodiments, the delivery can be surgical implantation of a composition described herein. In some embodiments, the delivery can be one of extravascular delivery, injection or catheter based injections; intravascular delivery, injection or catheter based injections; intravenous delivery, injection or catheter based injections; intraarterial delivery, injection or catheter based injections; intrathecal delivery, injection or catheter based injections; intraosseous delivery, injection or catheter based injections; intracartilaginous delivery, injection or catheter based injections; or intravesical delivery, injection or catheter based injections.

In some embodiments, a delivery of composition described herein to a mammalian subject can be delivery via mechanical pumps with percutaneous or implantable catheters. In some embodiments, a delivery of composition described herein to a mammalian subject can be catheter based delivery to any area/organ in the body.

In some embodiments, a delivery of composition described herein to a mammalian subject can be delivery via expanded dispersion through various devices promoting increased tissue penetration or wider tissue distribution (e.g., ultrasound, iontophoresis, heat, pressure, etc.)

Examples

The following example illustrates, but not to limit the claimed invention.

1. SNell-1

An optional open reading frame in exon 7 within 240 amino acids from the first open reading frame (ORF) that lacks the TSP1-N like domain in silico search was identified. The ATG potential translational start site for SNell-1 site is located within exon 7 of LNell-1 and the promoter sequences for SNell-1 are within intron 2 of LNell-1. Based on 5' RACE and sequencing results, the existence of the predicted short form was further demonstrated. Independent work by Database of Transcriptional Starting Sites (http://dbtss.hgc.jp) using 5' Oligo-Capping method also identified a clone with the same alternative form for SNell-1.

Figure 2:
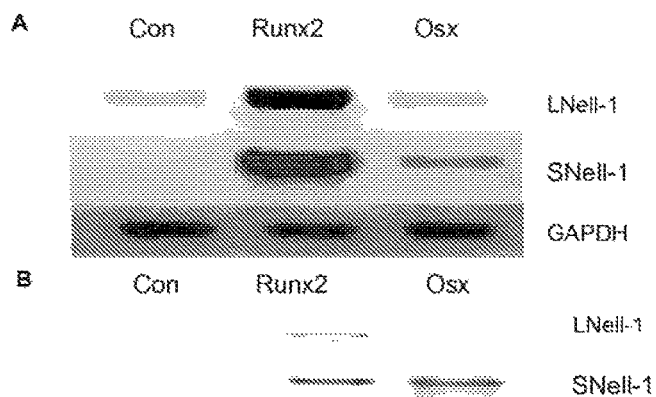
FIG. 2 shows LNell-1 and SNell-1 expression after Osx and Runx2 transfection in NMCCs. Mouse primary cells were transfected with control (Con), Osx and Runx2 plasmids. 48 hours after transfection, RNA samples were extracted for RT-PCR and medium collected for immunoprecipitation (IP) assay using Nell-1 C-terminal Ab cross-linked with protein G beads. (A) RT-PCR results after using LNell-1 or SNell-1 primers. (B) IP results using C-terminal Nell-1 antibody recognizing both LNell-1 and SNell-1.

SNell-15' primer was designed based on its 5' UTR sequence. When transfected with Osx, the PCR product using N-terminal primers (specific for LNell-1) was significantly downregulated (coinciding with the promoter result), while the PCR product using SNell-1 specific primers was significantly elevated above control (FIG. 2). In contrast, Runx2 transfection upregulated both LNell-1 and SNell-1 transcripts.

LNell-1 contains 810 aa with a molecular weight of 89.5 kD (~120 kD after post-translational modification); the predicted size for SNell-1 is 570 aa with a molecular weight of 62.5 kD.

To further verify the existence of this smaller isoform, the media from Osx transfected NMCCs was collected. It was shown that Osx downregulated LNell-1 and increased the expression of an ~70 kD SNell-1 protein that is consistent with the predicted nonglycosylated weight of 62.5 kD (FIG. 2). Similar results were obtained using Saos2 cells.

2. Functional Role of SNell-1 in Skeletal Development

A Nell-1 gene-trapped ES cell line was used to generate general and tissue specific [Col1α1-Cre-(osteoblastic) and Col2α1-Cre (chondrogenic)] Nell-1 knockouts. LNell-1 and SNell-1 overexpressing mice were generated. In addition to comprehensive morphological and histological examination, levels of Runx2 and Osx expression were further examined on the different Nell-1 expression backgrounds by immunohistochemistry.

Given the important roles of Runx2 and Osx during skeletal development, SNell-1's effect on Runx2 and Osx expression were studied. Because phosphorylation status can affect Runx2 and Osx activity and because LNell-1 has been demonstrated to increase Runx2 phosphorylation and activity, SNell-1's effects on Runx2 and Osx phosphorylation status and activity were studied.

SNell-1 is normally expressed by late-stage osteoblasts. Excessive SNell-1 may induce more significant cellular apoptosis and greater inhibition of cell proliferation than LNell-1, with accelerated bone formation relative to WT mice, but decreased total bone formation relative to LNell-1 overexpression mice.

In terms of chondrogenesis, SNell-1 (which Runx2 and Osx upregulates and which reciprocally upregulates Runx2 and Osx mRNA) promotes early chondrocyte differentiation, with possible inhibitory effects on terminal chondrocyte differentiation.

The differential effects of LNell-1 vs. SNell-1 in Saos-2 cells were examined. Saos-2 transfected with pcDNA3.1-SNell-1 demonstrated increased Runx2, Osx, and Oc expression by day 6 of culture. In contrast, LNell-1 transfected Saos-2 cells demonstrated no change in Runx2 transcription (consistent with our previous data in MC3T3-E1), transiently increased Oc expression, and marked decrease in Osx expression (FIG. 3).

Figure 3:
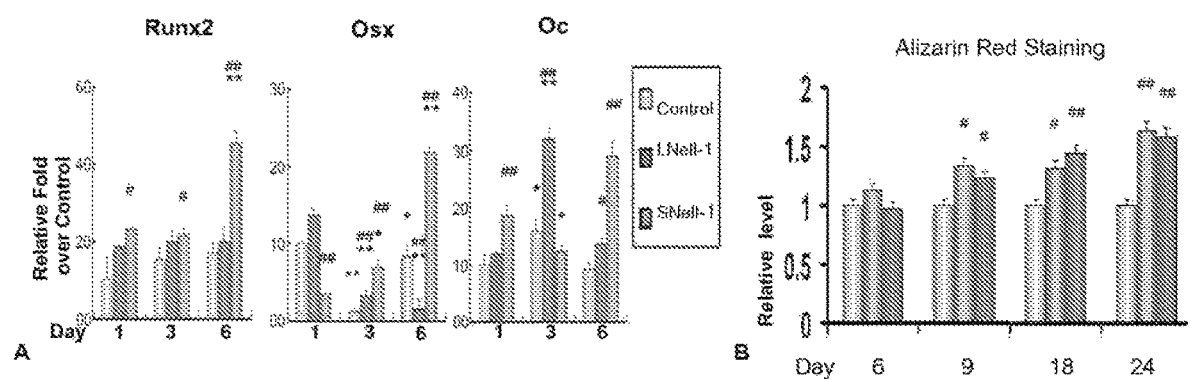
FIG. 3 shows the effects of LNell-1 and SNell-1 on Runx2, Osx, Oc expression and mineralization.

FIG. 3 shows the effects of LNell-1 and SNell-1 on Runx2, Osx, Oc expression and mineralization. FIG. 3(A) shows that Saos2 cells were transfected with pcDNA3.1 (Control), pcDNA3.1-LNell-1 or -SNell-1 for 24 hours and then exposed to osteogenic differentiation medium. mRNA expression of Runx2, Osx and Oc was analyzed by real-time PCR. $*p<0.05$, $**p<0.01$ compared to data of day 1 within same group. $\#p<0.05$, $\#\#p<0.01$ compared to control group within same time point. FIG. 3(B) shows Lentiviral transfection. Both LNELL-1 and SNell-1 show significant mineralization compared to control. $\#p<0.05$.

Figure 4:
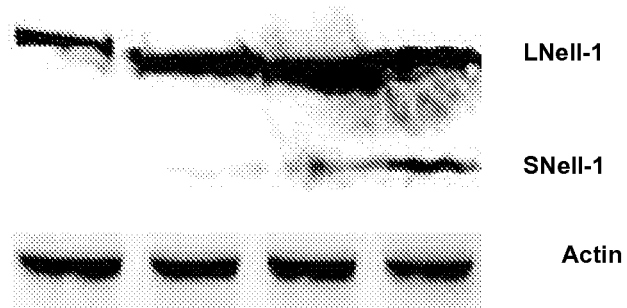
FIG. 4 shows LNell-1 and SNell-1 protein express patterns in mice heads.
Figure 5:
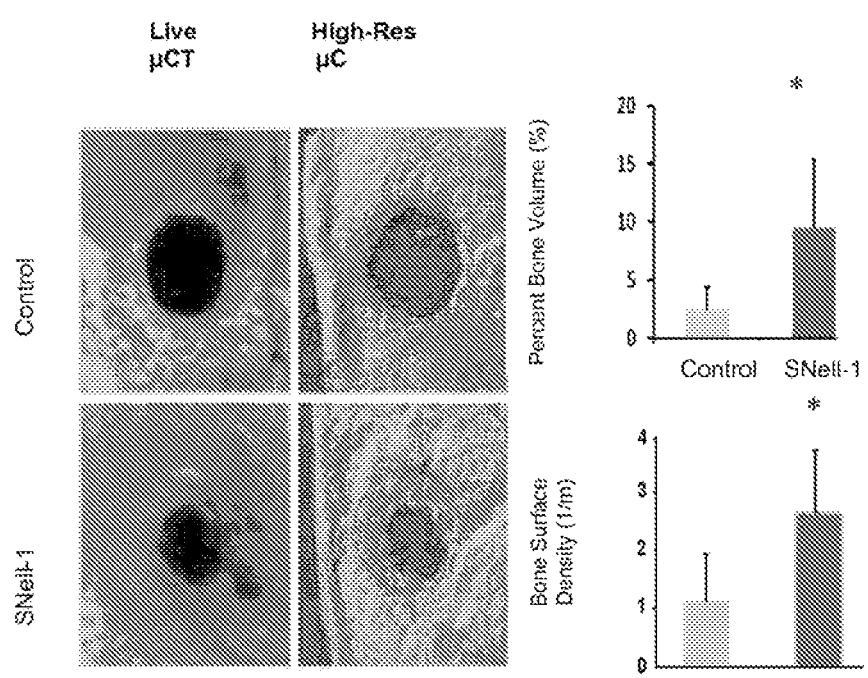
FIG. 5 shows calvarial defect healing with SNell-1.

SNell-1 was expressed during skeletal growth (FIG. 4) and formed bone when applied to calvarial defects (FIG. 5). FIG. 4 shows LNell-1 and SNell-1 protein express patterns in mice heads. LNell-1 is known to be highly expressed in brain tissues and is consistently expressed during and after gestation while SNell-1 is predominantly expressed postnatally.

FIG. 5 shows Calvarial defect healing with SNell-1. SNell-1 lentivirus (5M virus particles per site) embedded in collagen coated PLGA scaffolds were implanted onto 3 mm calvarial defect in athymic rats. Live μCT were taken at 2 weeks and high resolution μCT taken at 4 weeks. BV/TV and bone surface density both showed that SNell-1 induced significantly more bone formation ($*p<0.05$).

These data demonstrate that SNell-1 exhibits potent osteoinductive capability. It was found that isoform Nell-1 peptides are required for normal skeletal development and that isoform Nell-1 peptides are key components in the Runx2 and Osx regulatory network controlling osteoblastogenesis and terminal chondrocyte differentiation.

LNell-1 may be involved in earlier-stage and SNell-1 in later-stage osteoblastogenesis, and the converse for chondroblastogenesis (i.e., LNell-1 may be involved in later-stage; SNell-1 in earlier-stage). LNell-1 (upregulated by Runx2 and downregulated by Osx) may promote earlier stage osteoblast differentiation and less mature bone formation, while SNell-1 (upregulated by Osx and Runx2) may promote later stage osteoblast differentiation and more mature bone formation.

Conversely, for chondrocytes, Runx2 upregulated LNell-1 may promote terminal chondrocyte maturation (given the known roles of Runx2 in promoting chondrocyte hypertrophy) and Osx/Runx2 upregulated SNell-1 may have minimal or perhaps even inhibitory effects on terminal chondrocyte differentiation (given the known inhibitory effects of Osx on chondrocyte hypertrophy).

These data suggest that SNell-1 can lead to safer and more effective osteoinductive therapies.

3. Isoform Nell-1's Effects on Runx2 and Osx Phosphorylation and Activity

Coordinated regulation of Runx2 and Osx activity are crucial for bone formation. Studies by the present inventors suggest that LNell-1 and SNell-1 are important, not only as target genes for carrying out Runx2 and Osx functions, but that LNell-1 and SNell-1 are important for modulating Runx2 and Osx expression and activity during cell differentiation. Understanding of isoform Nell-1's function and mechanism will lead to improved and safer therapeutic approaches to conditions related to bone formation.

The effects of isoform Nell-1 on Runx2 phosphorylation status were examined and correlated with Runx2 activity. Runx2 activity was quantitated physiologically by osteoblastic marker expression, and directly by luciferase reporter systems that serve as direct readouts of Runx2 activity.

Because LNell-1 increases Runx2 phosphorylation through involvement of mitogen-activated kinase signaling (MAPK) cascades, and contains a conserved TSP1-N/LG-like domain that may interact with cell-surface integrins to activate MAPK pathways, the relative levels of MAPK and focal adhesion kinase (FAK) activation by LNell-1 and SNell-1 were also examined.

LNell-1 and SNell-1 exerted different effects on Runx2 and Osx phosphorylation and activity with correspondingly different effects on osteogenic and chondrogenic differentiation.

The effects of single or combined Nell-1 isoforms on Runx2 and Osx phosphorylation status and corresponding bioactivities were also examined. Combined LNell-1 and SNell-1 can synergistically increase Runx2 activity and osteoblast differentiation and therefore provide a combined therapy.

4. Isoform Nell-1' Effects on Bone Formation In Vivo

The osteoinductivity of LNell-1 and SNell-1 in a calvarial defect model and a bone marrow stem cell (BMSC) implant model were examined.

Both Runx2 and Osx are known to promote osteoblast lineage commitment and maturation. However, while Runx2 promotes terminal chondrocyte differentiation, Osx inhibits this process. Osx-induced SNell-1 will preferentially promote an intramembranous ossification-like process of direct osteogenesis (i.e., mesenchymal stem cells differentiating into osteoblasts), while LNell-1, which is specifically upregulated by Runx2 and downregulated by Osx, can preferentially promote a more endochondral ossification-like process of step-wise osteogenesis (e.g., mesenchymal stem cells differentiating into chondrocytes with formation of calcified matrix, followed by vascular invasion and influx of new mesenchymal stem cells that then differentiate into osteoblasts).

It is expected that combined LNell-1 and SNell-1 therapies are more efficacious for bone growth at lower doses—allowing further optimization of Nell-1 safety and efficacy. The BMSC study will also determine how to use the two isoform Nell-1 peptides as novel molecular tools to control bone vs. cartilage formation in healing bone fractures so that development of excessive cartilage in the fracture callus can be minimized and direct, or step-wise, bone formation maximized.

To determine the relative osteoinductive and chondroinductive properties of LNell-1 vs. SNell-1 vs. combination LNell-1/SNell-1 in complex in vivo environments, two models were used—an established calvarial defect model of intramembranous bone regeneration that does not form chondroid bone and a BMSC implantation model that more closely resembles endochondral bone regeneration with osteochondral bone formation. Quantitative and qualitative bone formation was evaluated at gross morphologic, histologic, and molecular levels.

The osteoinductive properties of rhLNell-1 vs. rhSNell-1 in an intramembranous ossification model were studied. Previous data indicates that LNell-1 can accelerate both chondrogenesis and osteogenesis. In contrast, SNell-1, unlike LNell-1, can primarily promote osteoblastogenesis with minimal (or perhaps even inhibitory effects) on terminal chondrocyte differentiation. It is expected that SNell-1 will induce faster and more mature bone which manifests as increased bone volume/density, increased or earlier expression of osteoblastic marker genes, and/or more mature bone trabecular patterns on histology.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

We claim:

1. A synthetic bone graft material comprising an isolated polypeptide comprising a naturally occurring human, rat, or mouse neural epidermal growth factor-like (EGFL)-like-1 (Nell-1) polypeptide that extends from the beginning of the first chordin-like cysteine-rich domain to the end of the fifth chordin-like cysteine-rich domain, wherein the isolated polypeptide lacks the N-terminal thrombospondin-1 (TSP1) domain of a naturally occurring Nell-1 polypeptide.

2. The synthetic bone graft material of claim 1, wherein the synthetic bone graft material further comprises a pharmaceutically acceptable carrier.

3. The synthetic bone graft material of claim 1, wherein the synthetic bone graft material further comprises a naturally occurring Nell-1 polypeptide.

4. The synthetic bone graft material of claim 1, wherein the synthetic bone graft material further comprises a biocompatible matrix, a polymer, a bone morphogenic protein (BMP), collagen, or demineralized or mineralized bone powder or granules, or is combined with a prosthetic device.

5. The synthetic bone graft material of claim 4, wherein the biocompatible matrix comprises a cell expressing the isolated polypeptide.

6. The synthetic bone graft material of claim 4, wherein the synthetic bone graft material, biocompatible matrix, or polymer is resorbable.

7. The synthetic bone graft material of claim 4, wherein the polymer is a biodegradable polymer or a biostable polymer.

8. The synthetic bone graft material of claim 4, wherein the synthetic bone graft material, biocompatible matrix, or polymer comprises a cell adhesion molecule.

9. The synthetic bone graft material of claim 4, wherein the synthetic bone graft material comprises bioglass or a bioceramic.

10. The synthetic bone graft material of claim 4, wherein the BMP is BMP-2.

11. The synthetic bone graft material of claim 1 wherein the isolated polypeptide is formulated for sustained release.

12. The synthetic bone graft material of claim 1, wherein the synthetic bone graft material is formulated for administration to a human.

13. The synthetic bone graft material of claim 1, wherein the synthetic bone graft material is formulated for delivery by in situ implantation, local administration, injection, direct injection through a surgically opened site or a trauma site, surgical implantation, intraosseous delivery, intraosseous injection, intraosseous catheter based injection, intracartilaginous delivery, intracartilaginous injection, intracartilaginous catheter based injection, or expanded dispersion through a device that increases tissue penetration or promotes wider tissue distribution.

14. The synthetic bone graft material of claim 1, wherein the naturally occurring Nell-1 polypeptide has the sequence of SEQ ID NO: 3.

15. The synthetic bone graft material of claim 1, wherein the isolated polypeptide has the amino acid sequence of the carboxy-terminal domain of the Nell-1 polypeptide having the amino acid sequence of SEQ ID NO: 3.

16. The synthetic bone graft material of claim 1, wherein the isolated polypeptide has the amino acid sequence of SEQ ID NO: 1.

* * * * *